United States Patent [19]

Vaseen et al.

[11] 4,375,812

[45] Mar. 8, 1983

[54] BURN TREATMENT BY PATIENT IMMERSION IN AN INERT, ISOTONIC LIQUID, WHICH HAS HAD OZONE ABSORBED THEREIN

[76] Inventors: Vesper A. Vaseen, 9840 W. 35th Ave., Wheatridge, Colo. 80033; Dale A. Vaseen, 6911 Kendall St., Arvada, Colo. 80003

[21] Appl. No.: 238,217

[22] Filed: Feb. 26, 1981

[51] Int. Cl.³ .............................................. A61M 15/08

[52] U.S. Cl. ........................... 128/207.27; 128/202.25; 128/202.12; 128/202.14

[58] Field of Search ................................ 128/365-370, 128/202.12, 202.14, 207.27, 202.25

[56] References Cited

U.S. PATENT DOCUMENTS

| | | | |
|---|---|---|---|
| 3,366,110 | 1/1968 | Gaylord | 128/369 |
| 3,402,243 | 9/1968 | Gerow | 128/369 |
| 3,404,678 | 10/1968 | Ardenne | 128/369 |
| 3,692,028 | 9/1972 | Etten et al. | 128/369 |
| 3,815,595 | 6/1974 | Bar | 128/207.27 |
| 3,831,593 | 8/1974 | Ochoa | 128/369 |
| 4,149,536 | 4/1979 | Villard | 128/365 |
| 4,196,726 | 4/1980 | Ronzi | 128/207.27 |

FOREIGN PATENT DOCUMENTS

| | | | |
|---|---|---|---|
| 2398492 | 3/1979 | France | 128/367 |

*Primary Examiner*—Kyle L. Howell
*Assistant Examiner*—Daniel P. Burke

[57] ABSTRACT

The survival of a patient with an extensive burn is dependent upon the ability of the burn surgeon to keep the patient in a state of positive nitrogen balance, of immune competence, and in equilibrium with the bacteria colonizing his burn wounds until permanent closure of the wounds is accomplished with autogenous skin grafts. Immune competence and bacteria colonization are controlled by the method of immersing the patient in whole are in part, so as to immerse the burn wound in an isotonic, dielectric, inert, halogenated hydrocarbon liquid, which is selected with a specific gravity greater than the patient. The liquid is kept sterile by absorbing therein ozone, along with cleaning, filtering and heat sterilization. The ozone controls the bacteria colonization whereas the density of the liquid resists loss of cell moisture thus assisting the immune competence and control of a positive nitrogen balance.

7 Claims, 1 Drawing Figure

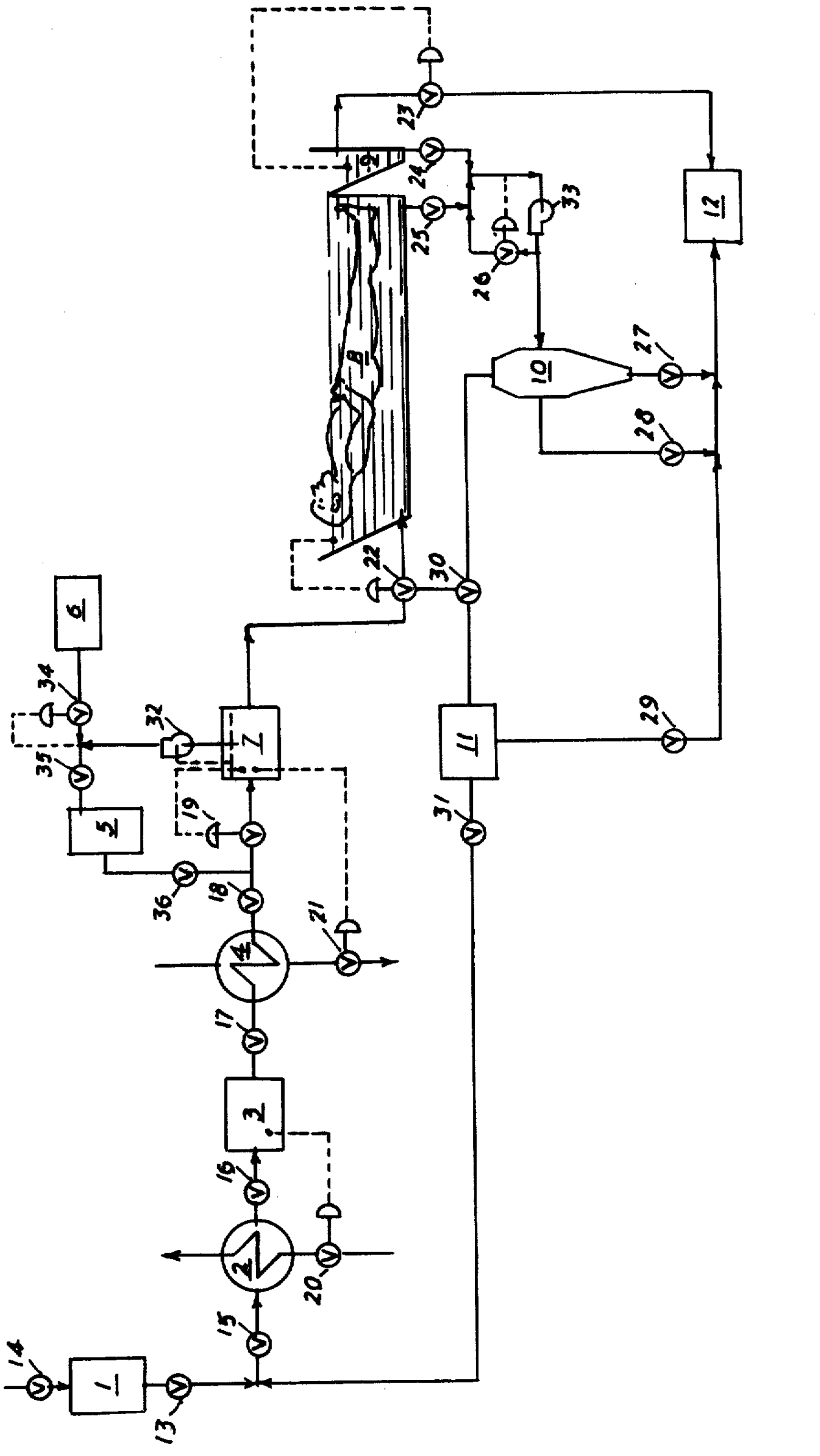

BURN TREATMENT BY PATIENT IMMERSION IN AN INERT, ISOTONIC LIQUID, WHICH HAS HAD OZONE ABSORBED THEREIN

DESCRIPTION OF PRIOR ART

The survival of a patient with extensive burn is dependent upon the ability of the attending burn surgeons and staff in keeping the patient in a state of positive nitrogen balance, of immune competence, and in equilibrium with the bacteria colonizing his wounds until permanent closure of the wounds is accomplished; such as with autogenous skin grafts. Failure to accomplish these ends increases the risk the patient will succumb from fatal complications—some of which are: malnutrition, protein depletion, disseminated intravascular coagulation, septicemia, subacute endocarditis, pneumonia, pyelonephritis, ulceration of the gastrointestinal tract, adrenal depletion, pulmonary infection, and toxic myocarditis.

Patients who are able to ingest and digest adequate nutrition and are maintained in a state of immune competence during the three to five weeks of required aggresive wound care rarely succumb to their thermal injuries.

This invention relates principally to the initial wound care and management. Wound evaluation must be carried out in a clean environment by personnel appropriately attired to protect the patient from contamination by as few bacteria as possible.

Appraisal of the burn depth and extent is best accomplished by inspection after all blisters, loose, and non-viable tissue have been removed. Removal is usually by using sterile disposable straight razor(s). A wide margin of normal skin surrounding the burn wound should be shaved to prevent contamination later from hair follicles.

An apron should be worn by all personnel when working with patients with open wounds. The apron disposed of immediately on leaving the patient. Photographs should be taken to be used for comparison as wounds close.

Initial wound cultures should be taken in the admitting room for qualitative and quantitative analysis.

The method of wound care, prior to this invention were: exposure therapy, occlusive dressings, open dressings and excisional therapy. Exposure therapy is to control bacterial colonization without the aid of topical agents by using light and a cool environment. Exposure treatment is particularly suitable for burns of the face and perineum, unilateral burns of the trunk and limbs, and extensive burns that cannot be adequately dressed.

The patient is rested on a clean, dry, sterile sheet with total burned area completely exposed. Following a "crust" formation, usually in 24 to 36 hours, the wound is protected against bacterial contamination, by the crust, from the surrounding environment.

Occlusive dressings are indicated when patients require being moved from one treatment center to another. Their use assures protection from bacterial contamination and the maintenance of the position of function for burns of the extremities, immobilization of the joints, and the prevention of post-burn contractures.

The inner layer of the occlusive dressing should consist of a non-adhesive or non-adherent layer of a topical antimicrobial agent impregnated into fine mesh gauze. The topical agents that are normally used in conjunction with occlusive dressings are: silver sulfadiazine, gentamicin, nitrofurazone, and povidone-iodine. Mefenide acetate should not be used since its absorption is increased under these circumstances. The occlusive dressings should be changed at a frequency of every two to three days until the burn wound has healed or is ready for skin or skin substitutes grafts.

Wet dressings, a form of occlusive dressing, tend to produce a separation of non-viable tissue, reduce cellulitis, and hasten the preparation of the burn wound for grafting. The application of normal saline compresses, removed every eight hours, is an effective treatment modality to accomplish these ends.

The open method of wound care is best defined as the treatment of the burn wound by exposure and a topical agent. This is the most popular method of therapy now being used to treat burn wounds. There are several advantages with open therapy, the most advantageous being case of wound examination and evaluation. Early physical therapy is possible due to freedom of motion of members. Body temperature is more easily adjusted providing patient comfort.

Disadvantages to open therapy are a delay in eschar separation, prolonging the period during which the patient is at risk to invasive burn wound sepsis, significant discomfort from topical agents applied to the burn wound, chilling of patient from loss of body heat, and severe hypothermia resulting from prolonged exposure during patient moves from treatment area to another.

Excisional therapy is to remove all non-viable tissue down to a viable base. This prevents septic complications, minimizes prolonged metabolic stress, and favors early and rapid rehabilitation. The invention disclosure herewith does not replace, but is an assist to bacterial contamination, and reduced blood loss; thus equally applicable to excisional therapy. Procedures and techniques for excisional therapy are well publicized and known to those familiar with burn wound treatment; and therefore, not covered in greater detail herein.

The invention disclosure herein reduces all burn wound treatment to the "open method" with all its advantages, and elimination of most of its disadvantages.

REFERENCES

Surgical Clinics of North America, Vol. 58, No. 6, December 1978: Closing the Burn Wound; Bruce G. MacMillanm M.D.; Chief of Staff, Shriner's Burn Institute, Cincinnati Unit; Shrine Professor of Surgery, University of Cincinnati College of Medicine, Cincinnati, Ohio.

Surgical Clinics of North America, Vol. 57, No. 5, October 1977: Management of Burns; Donald H. Parks, M.D., F.R.C.S(C)*; Hugo F. Carvajal, M.D.; and Duane L. Larson, M.D., *Assistant Professor of Surgery, University of Texas, Medical Branch; Chief of Surgery, Shriner's Burn Institute, Galveston, Texas.

U.S. Pat. Nos. 4,049,398: Sept. 20, 1977; Vaseen—Separating Oxygen from Air; 4,140,608; Feb. 20, 1979; Vaseen—Producing Ozone via Corona; 4,150,956: Apr. 24, 1979; Vaseen—Producing Medical Grade Oxygen; 4,182,663: Jan. 8, 1980; Vaseen—Producing Ozone via U.V.; 4,232,665: Nov. 11, 1980; Vaseen—Portable Lung Machine.

Science News Magazine; Vol. 18; 1980; Ozone: Pollutant Slows Cancer Growth.

SUMMARY OF THE INVENTION

This invention eliminates or reduces the need to use occlusive dressings and topical agents; extending the advantages of "open" burn wound care and treatment. The method of "open" burn wound treatment art and science taught herein consists of the use of an isotonic, dielectric, inert, halogenated hydrocarbon liquid as the "bed" or "body support" mechanics for the burn patient in total or in part by specific members. The Patient, if the burn wounds are on the thorax, the upper extremities, trunk, lower extremities, or back of the head, is "floated" in the above liquid in a bed/bath, with the burn wound completely submerged in the liquid. Although usually it is preferable to have first surgically removed all blisters, loose and nonviable tissue, and have made a burn wound appraisal, then immerse the patient, where hypothermia or bacterial contamination are a major factor, the nude patient is immediately placed in the inert liquid bed/bath.

The drawing outlines a suggested flow sheet and recommended appurtenant apparatus required for retaining the integrity of the inert liquid.

The inert liquid is heated to sterilization temperature by preferably a heat exchanger (2), then retained in a sterile reservoir for the length of time and combination of temperature, pressure and time are found by laboratory control to provide the degree of bacterial removal specified by the Burn Surgeon.

Prior to use, the hot, sterile inert liquid is cooled by preferably a heat exchanger (4) to the temperature specified by the Burn Surgeon as best suited to the particular burn patient. Normally, this will range from 96° F. to 100° F.

An ozonator (5) is used to excite a fraction of a, preferably, medical oxygen supply to the ozone state. The ozone/oxygen mixture (gases) is added to the inert liquid through a mixer (not shown), preferably a venturi throat type; thence the oxygen/ozone as absorbed in the inert liquid is stored for immediate use in a storage reservoir (7).

The bath/bed (8) is now filled with the inert liquid at a temperature of from 96° F. to 100° F. to the maximum liquid level which is controlled by a H.L.L. Valve. The system is completely filled with the inert liquid, with a pump (33) returning overflow liquid from recycle sump (9) through the separator centrifuge (10) then filter (11), and back to sterilizer heater.

The liquid is allowed to recirculate until in equalibrium as to both flow rate and temperature selected.

The burn patient is, preferably nude, carefully placed in the bed/bath using disposable restrains to support the head in a positive manner with the face out of the liquid; and similar disposable restraints to submerge the entire body, or those burn members under the inert liquid surface. Since the specific gravity of the body or members of the burn patient is normally from 1.0 to 1.2 and the specific gravity of the inert liquid exceeds this range, even up to 2.0, the body will "float" unless restrained under the liquid. Burn wounds on the back, if restricted to the back, may be submerged by the depth of float of the body with minimal additional restraints, except for those required to protect the patient from turning over during sleep. The reverse is true for chest and abdomen.

Extremities can be treated by individual member immersion, or by construction of a special bath/bed facility for such specific use, not shown herein on the drawing.

The burn patient is thereafter treated in much the same manner with exposure therapy or as with occlusive therapy.

The Burn Surgeon removes any additional non-viable tissue without removing the burn patient from the bed/bath.

Liquid discharged from the burn patient wounds is immiscible with the inert liquid and is rejected from the liquid to float on the top of the bed/bath. This should be coaxed to the bed/bath overflow and collected in the recycle sump (9) where it is removed to incineration.

The absorbed ozone in the inert liquid is measured periodically, preferably hourly, and adjustments made to the oxygen flow rate to retain the ozone concentration within specified limits.

Urine passing should be collected, preferably by catheter, and disposed of as per hospital regulations.

Bowel movements should take place outside the bed/bath by bed pan or stool, if at all possible.

Both urine and fetal material, if accidently passed to the inert liquid, are immediately rejected to the liquid surface, where they can be removed to the recycle sump (9).

Both the apparatus required and the method of treatment should be conducted throughout in a "clean room", specifically designed for this purpose. Ventilation of the clean room should be constantly monitored for ozone and oxygen content.

PREFERRED EMBODIMENT

The teaching of the art and science of this invention disclosure is best done by way of example. The example herein used is based on the entire body of a burn patient requiring the treatment and burn wounds closing on the entire body surface, both front and rear. Since this invention disclosure is only one phase of the entire treatment program, that being the initial wound closing phase, only this phase of treatment is presented. Surgeons and their staff knowledgeable and trained in management of burns and closing the burn wound will know the proper treatment required on admissions of the burn patient, and treatment prior to closing of the wound, as well as following the closing of the wound.

This disclosure teaches the art and science of an alternative treatment method and procedure to both occlusive dressings along with topical agents, as well as the open method.

The method is used in conjunction with the total management of the burn wound patient. First, the burn is classified as to agent and depth, along with the regular hospital care. This usually consists of the insertion of an intravenous line, insertion of an indwelling urinary catheter, insertion of a nasogastric tube, removal of all burned clothing and first aid dressings, along with obtaining a base-line hematologic and biochemical parameters including carboxy-hemoglobin and blood gases, if inhalation is suspected.

The burn injury initiates rapid and major fluid electrolyte shifts. Successful resuscitation also depends on controlled, monitored fluid replacement to avert "burn shock". Resuscitation fluid administration and servicing methods are fully explained in various medical texts and published papers; therefore, those surgeons and their staffs, so knowledgeable in their field will have no difficulty determining this phase of the burn patient's treatment. The inert liquid bed/bath treatment as taught by this disclosure will assist in the resuscitation fluid control and servicing by nature of the liquids physical properties. The isotonic liquids used have a specific gravity greater than (1) one, preferably ranging from 1.1 to 2.0. The compressive effect of the "heavy" liquid on the open burn wound resists loss of cell moisture, at the same time rejecting it by floatation, thus resisting edema formation and the subsequent proteinaceous edema fluid buildup which provides a mechanism for bacterial colonization at the site of the wound. The "heavy" liquid compressive effect also assists in the control of antidiuresis, primarily by decreasing the loss by secretion of antidiuretic hormone.

Nutrition requirements of the burn patient are well known procedures to those surgeons and their staffs, and are not usually influenced by the immersion bed/bath treatment herein disclosed, except as would effect the bowel movement frequency of the patient being treated. Diet should be adjusted and controlled to resist or inhibit bowel movements for the normal duration of the immersion bed/bath treatment—normally two to three days.

At the point in the treatment of the burn wound patient wherein the conventional treatment of "exposure therapy", "occlusive dressings", "open dressings" and "excisional therapy" is the next phase, the inert liquid bed/bath is used to replace all but the "excisional therapy".

The inert liquid bed/bath is prepared for the burn wound patient as soon as the surgical team has made its assessment of the extent of injury and has made the decision to use the "immersion" treatment.

The inert liquid immersion bed/bath method of treatment is based in part on the medical factors of the reaction of ozone on healthy vs. sick cells; as well as the bacteriacidal effect of ozone on all bacteria. With ozone concentrations as high as 0.8 ppm, cancer (sick) cells are inhibited up to 90%, whereas normal (healthy) cells are inhibited less than 50%. Ozone concentrations for bactericidal control are from 0.01 ppm to 5 ppm, but preferably at 0.4 ppm. This is reduced or increased as laboratory reports provide bacterial colony growth is restricted to levels commensurate with the burn wound closing and the surgeons' appraisal of what is a satisfactory level of bacterial growth. Surgeons and their staffs, knowledgable in burn wound closing treatment, will have no difficulty in making these determinations.

The inert liquid bed/bath treatment is carried on in a "clean room" environment. Surgeons and their staff will have no difficulty in determining the status of what the term "clean room" specifies. This example specifies the storage, sterlization, cooling and temperature control, ozonating, bed/bath use; liquids/solids separations by gravity-centrifuge and filter; thence recycle; for a single bed/bath; of these facilities only the bed/bath is required to be in the "clean room"; although it is allowable to "clean room" house the entire apparatus. Although this specification, by way of example, alludes to a single bed/bath system; it is not meant to exclude the combining of more than one system into a common reclamation and sterilization system for more than one bed/bath; separating the flow of the sterile, temperature adjusted, inert liquid, to more than one individual bed/bath.

The system of treatment for the inert liquid to preserve its integrity for use consists of a receiving tank or reservoir (1) which is filled initially with sufficient inert liquid as to not only fill the system components but to also replace attrition and spill losses during each patient treatment duration; normally two to three days. For Example, with a bed/bath designed for seven (7) feet (2.134 meters) in length; two and one half (2½) feet (0.762 meters) wide and with a liquid level depth of two (2) feet (0.61 meters) (without the patient being immersed) the inert liquid required is 262 gallons. Recirculation of the entire system ranges from zero to twenty (20) times per hour, but preferably once per hour. Flow control is accomplished by a re-recirculation pump (33) acting in concert with an automatic bypass valve (26) and an inert liquid bed/bath liquid level control valve (22).

Sterilization is accomplished by heating the recirculating inert liquid in the closed system by passing it through a heater (2) with a capacity to raise the temperature of the liquid from ambient at 70° F. (21.11° C.) to 500° F. (260° C.); but preferably to 250° F. (121.11° C.) when sterilizing twenty two (22) gallons each five (5) minutes. The hot inert liquid is retained in a sterilizer tank or vessel (3) at, preferably 250° F. (121.11° C.) for from zero to thirty (30) minutes; but preferably for five (5) minutes. In this example the sterilizer vessel retains the 250° F. (121.11° C.) hot liquid for five (5) minutes, thus obligates twenty two gallons of liquid. The sterilizer vessel is a superatmospheric vessel, designed for operation at zero (0) to ten (10) atmospheres pressure, but preferably at two (2) atmospheres when sterilizing at 250° F. Sterilization temperature and pressure combination is preferably such that the water remaining, if any, in the inert liquid is evaporated out of the system, and vented to atmosphere from the sterilizer vessel (3). Vent is not shown on the drawing.

The sterilizer heater is preferably an electric heated heat exchanger type with a rating of 5,000 BTUs per minute, to be operated at 3,000 BTUs per minute when sterilizing twenty-two (22) gallons each five (5) minutes at two (2) atmospheres and 250° F.

The liquid is, following sterilization, passed through a cooler, heat exchanger, (4) wherein the temperature of the hot sterilized inert liquid is cooled to "use" temperature. "Use" temperature is the temperature selected by the surgeon in charge as best for the particular patient. Normally, the "use" temperature is body normal temperature of 96° F. (35.56° C.) to 100° F. (37.78° C.).

Manual valves (15) & (16) isolate the sterilizer heater (2) with a temperature controlled valve (20) adjusting the heat supplied to the heater (2) to retain the integrity of the sterilization temperature in vessel reservoir (3).

The sterilized, inert liquid, as cooled to the surgeon's specified "use" temperature is passed through a mixer such as a venturi throat (not shown on the drawing) wherein a mixture of ozone in oxygen gas is absorbed in the inert liquid as it collects in the storage reservoir (7) for immediate service to the bed/bath (8). Preferably, the storage reservoir (7) is elevated to allow gravity drainage of the inert liquid to the bed/bath (8); thus allowing excess oxygen gas not absorbed in to the liquid to collect over the liquid therein and be removed preferably by pump (32) for recycle use.

The inert liquid flow through the cooler-heat exchanger (4) is isolated by valves (17) & (18) with the integrity of the specified temperature in the storage reservoir controlled by a temperature sensor controlling a temperature controlled valve (21) which increases or decreases the flow of cooling fluid removing the heat.

The storage reservoir capacity ranges from zero gallons to 262 gallons, but preferably, as per this example, for ten (10) minutes' supply or 44 gallons.

The total inert liquid supply is, for this example; sterilizer, 22 gallons; storage reservoir, 44 gallons; bed/bath, 262 gallons; with system piping and appurtenances, 12 gallons; thus a total system of 340 gallons.

The inert, isotonic liquid, is preferably a perfluorocarbon; that is a completely flourinated organic compund derived from common organic compounds by replacement of all carbon bound hydrogen atoms with flourine atoms.

Combinations of flourocarbons with other non oxidizable combinations are equally satisfactory such as those similar to $(C_4F_9)_3N$. The inert, isotonic liquid selected has the general physical properties of being extremely non-polar with low solvent action; colorless; odorless; non-toxic, (acute toxicity ($LD_{50}$):133 ml/kg in rats and 45 ml/kg in mice), and non-flammable. They also have high thermal stability, practically no chemical activity, and leave essentially no residue. For example, the selection of a liquid $(C_4F_9)_3N$ provides a liquid with the following physical characteristics:

| | English | Metric |
|---|---|---|
| Boiling Point | 311° F. | 155° C. |
| Density (25° C.) | 115#/$^3$ | 1.85g/cm$^{-3}$ |
| Kinematic Viscosity (25° C.) | 2.4 cs | 2.4 cs |
| Vapour Pressure | 0.058#/in$^2$ | 3 Torr |
| Specific Heat | 0.25 BTU/# | 0.25 cal/gram °C. |
| Heat of vaporization | 31 BTU/# | 17 cal/g |
| Surface Tension - 25° C. | 0.0029Po Poundals/in. | 16 Dynes/cm |
| Solubility of Water - 25° C. | 7 ppm (wt) | 7 ppm (wt) |
| Solubility of air - 25° C. | 22 ppm (wt) | 22 ppm (wt) |
| Solubility of oxygen - 38° C. | — | 0.238g/1000g |

Those familiar with flourocarbon liquids will have no difficulty in specifying and obtaining commercially available inert, isotonic liquid for this use.

The ozonator (5) is any process and apparatus which converts oxygen to ozone. This can be by passing oxygen gas through a carbon arc, through a corona, a laser beam, or an ultraviolet light source. The ozonator is selected, as per this example, to convert oxygen molecules ($O_2$) to ozone molecules ($O_3$) from 0 to 5 grams of ($O_3$) ozone per hour; but preferably two (2) grams of $O_3$ per hour. The oxygen solubility of the inert liquid, if for example, $(C_4F_9)_3N$, is 495.51 grams of oxygen ($O_2$) per hour. The oxygen is preferably medical grade oxygen which is supplied by bottle (6) or hospital supply from bulk system. The oxygen flow rate is adjusted by automatic flow rate control valve (34) through the ozonator isolation valve (35) thence through the ozonator apparatus (5); thence through the isolation valve (36) into the mixer, such as venturi throat, where the inert liquid is saturated with oxygen—ozone gas mixture, prior to the influent entry to the storage reservoir (7). The example herewith provides a feed supply of inert liquid for the bed/bath (8) which is now 98° F. (36.67° C.); with 0.238 grams of oxygen per each 1,000 grams of liquid; or 495.51 grams of oxygen per hour of which two (2) grams or 0.40362% is ozone.

The bed/bath used in this example is for the whole body; however, specific baths or basins are just as usable when designed for specific burn wounds of specific parts or members of the body. The example herein illustrates a large bed/bath of 7 feet in length, 2½ feet in width, and 2 feet in depth; capable of a large (250 pound) man. Smaller bed/baths are equally applicable for small persons. It is not the intent of this example to establish any definite bed/bath size or configuration. The bed/bath containment unit conforms to standards of hospital equipment. Knowledge of said standards are well known to those practicing in the medical arts and sciences.

The purpose of the bed/bath is to support, by the liquid bouyancy, the torso and/or members of the patient; thus eliminating the need of bed and subsequent linen. The body and/or its members sustaining burn wounds is oriented in the bed/bath so as to immerse the burn wound(s) beneath the liquid surface at all times. This is accomplished by using disposable restraining straps or belts which are located against the body and/or its members in such a way as to not be in contact with the burn wounds. The support and retaining straps are preferably run laterally across the bed/bath as well as longitudinally the length of the bed/bath as required. The restraining straps or belts fastened to the bed/bath edges by meams of clamps or other binding devices or pipe rails. Those familiar with hospital equipment will have no difficulty in selecting and using such appurtenances to the bed/bath use. The drawing does not show these straps or clamps.

The inert liquid is added to the bed/bath until it overflows the weir which delivers the excess to the recycle sump (9). The recirculation pump (33) is started and the centrifuge (10) and filter (11) filled with the inert liquid. This requires isolation valves (30) & (31) be opened; with waste disposal valves (27) (28) & (29) being closed. With inert liquid now being returned to the head of the system at isolation valve (15) and the entire system filled, the patient is carefully placed in the bed/bath and the restraints adjusted to provide the maximum security against the face becoming immersed, as well as patient comfort.

The recirculation of the inert liquid is continued, preferably at a rate which will recycle the entire mass of inert liquid through the bed/bath and its appurtenant facilities once each hour. The sterilizer system, cooling and temperature control system, ozone/oxygen system, are monitored and adjusted as required to maintain the integrity of temperature and oxygen/ozone content of the system.

Prior to immersion of the patient, he should have had inserted an indwelling urinary catheter and have had the lower bowel vacated.

Fluids released from the open burn wounds due to escharotomy and removal of non-viable tissue, increased capillary permeability (water, electrolytes, and albumin); blood, protein plasma, antidiuretic hormone, etc.; although normally reduced in flow quantity due to the weight and consequent pressure of the inert support liquid on the open weeping cells, will to some extent continue until the open areas are initially healed and/or resurfaced with expanded autografts or temporary wound closure by one of the skin substitutes. This moisture released from the open burn wound, having a specific gravity near 1.0 as compared with the inert bed/bath liquid of from 1.1 to 2.0 and not being miscible with the inert liquid, is rejected to the surfact of the bed/bath.

The bed/bath immersion technique is used following each separate operation for removal of non-viable tissue and continued for the duration of time required for the open wound to recover to the extent of being healed or ready for grafts. The surgeon in charge will determine the extent of time per bed/bath immersion, and frequency of repeat treatment required based on the opinion as to the progress being made by each individual patient.

During each immersion treatment session, there is sluff of organic particulates, as well as possible surgical removal particulates; along with water bearing moisture materials; all of which will reject from the inert liquid and float on the surface. All floating materials not regularly skimmed from the bed/bath by the hydraulic flow through the structure are removed by manually working them to the "tail" end of the vessel and causing them to overflow the liquid depth control weir (shown on the drawing—but not numbered) to the recycle sump. The sump has an inert liquid level/water level interface level sensor which when the water based liquids and particulates builds up to a preset depth, activates the overflow valve (23) allowing these materials be drained directly to either a collection box or preferably an incinerator (12) for combustion disposal. The manual valve (24) at the effluent of the bed/bath can be alternately partially closed, then opened, to provide a greater flexibility of removal of the "skim" materials. The bed/bath drain valve (25) is normally closed, usually used only as a drain for the bed/bath.

The centrifuge (10) mechanically-gravity separates the remaining particulates and water bearing materials or fluids which were not separated in the gravity separator recycle sump (9). Both the solids and water bearing fluids are removed through drain valves (27) (28) to the waste collection box or preferably incinerator (12) for disposal.

The essentially pure inert liquid is then filtered to remove any solid less than 1.00$\mu$ (micron), but preferably less than 0.10$\mu$; with the filter material and solid solids collection passed through isolation valve (29) to the waste collection box or incinerator (12). During the period of time the filter is having a new filter, preferably cartridge type, installed, the filter is isolated from the system by isolation valves (30) (31).

The inert liquid, now pure, free of all but the normal solubility for water, and all particulate material per size of specification of filter required by the surgeon, is ready for recycle sterilization. Loss of inert liquid in the system is made up by transferring the new inert liquid volume required from the supply reservoir (1) by means of adding it to the supply tank through valve (14) and transferring it to the system through valve (13).

The remaining moisture retained in the inert liquid by nature of its solubility water, such as the 7 ppm per the $(C_4F_9)_3N$ used as the example herein, is evaporated in the sterilizer (3) and vented out of the system.

Although this disclosure has been by way of example for the method of immersion treatment of burn wounds, it is obvious the method is dependent on certain processing proceedures for the inert liquid, and thus although not an apparatus invention, is integrally coordinated with the various apparatus so as to process the inert liquid in concert with the operation of specific apparatus in order to satisfactorily use the treatment method.

Thus is may be seen that a patient suffering from a serious burn wound(s) can be during the total phase of his treatment treated by an immersion of the open burn wound in an isotonic, inert, liquid, with the advantages of: visual inspection of the wound at all times, aseptic environment over the wound at all times, loss of body moisture by weeping at the open wound reduced, tissue kept supple due to abstainance from dry air, surgical removal of eschar and non-viable tissue possible during immersion, body temperature control positive as per controlled bed/bath temperatures, physical confort of patient greatly enhanced by removal of any body weight on a solid surface (such as a bed sheet), elimination of frequent dressing changes with subsequent patient discomfort and bacterial infection hazards, elimination of frequent topical agent replacement with subsequent patient discomfort and bacterial infection hazards; and ease of convenience of exercise of patient's physical members. While the present invention has been described with a certain degree of particularity, it is understood that the selection of apparatus, and sequence of arrangement of the apparatus, and the quantities of materials used in the description has been made by way of example and that modifications in structures and details may be made without departing from the spirit thereof.

What is claimed:

1. A method of treating a burn wound patient by the immersion of the burn wound of a patient in an isotonic insert liquid in which the bactericidal agent, ozone, has been absorbed, comprising the steps of:

charging a closed system with an isotonic, non-miscible with water, inert liquid, wherein said liquid has a capacity to absorb oxygen/ozone gas combinations and said liquid has a specific gravity greater than 1.10, wherein said system contains, means for sterilizing said inert liquid, said sterilizing means comprising a natural gravity separation device, a mechanical gravity separation device, a filter and a heat sterilizer device, an ozonator for converting a fraction of an oxygen gas stream to ozone thereby forming an ozone/oxygen gas, an apparatus for mixing and said ozone/oxygen gas into said inert liquid, at least one bed/bath comprising a basin or open top vessel, in which said inert liquid is contained, adapted for the immersion of all or part of a patient's body members, except the face, therein, means for restraining a patient at a controlled submerged location in each of said at least one bed/bath and an overflow weir, appurtenant valves and controls to cause a temperature adjusted, quantity controlled flow through said at least one bed/bath, said flow causing the physical and gravitational rejection of water, water bearing liquid and other materials with specific gravities less than that of the inert liquid to the liquid surface where it is skimmed to said overflow weir, and immersing all or part of a burn patient's body members, except the face, for intermittent and extended periods of time into said inert liquid in said system for the treatment of open burn wounds.

2. The method of claim 1 wherein the said system is in a controlled aseptic environment.

3. The method of claim 1 wherein the said system further comprises means for the continuous control of a patient's body temperature.

4. The method of claim 1 wherein said restraining means are straps or belts which retain the torso or members thereof suspended in a predetermined position.

5. The method of claim 1 wherein said system provides for physical freedom of the burn wound patient and his members are exercised.

6. The method of claim 1 further comprising the step of surgically removing eschar and non-viable tissue while the patient is retained submerged in said inert liquid.

7. The method of claim 1 further comprising the step of nourishing the patient without the removal of the patient from the said bed/bath.

* * * * *